United States Patent [19]

Pastorino et al.

[11] 4,197,244

[45] Apr. 8, 1980

[54] CYCLIC PERKETALS AND THEIR USE FOR CROSS-LINKING HIGH DENSITY POLYETHYLENE

[75] Inventors: Ronald L. Pastorino, Larkspur; Roger N. Lewis, Martinez; Charles B. Abma, Davis, all of Calif.

[73] Assignee: Argus Chemical Corporation, Brooklyn, N.Y.

[21] Appl. No.: 929,754

[22] Filed: Jul. 31, 1978

Related U.S. Application Data

[60] Division of Ser. No. 772,407, Feb. 28, 1977, which is a division of Ser. No. 688,874, May 21, 1976, abandoned, which is a continuation-in-part of Ser. No. 591,783, Jun. 30, 1975, abandoned.

[51] Int. Cl.$^2$ .................. C07C 179/08; C07D 323/00
[52] U.S. Cl. ..................................... 260/338; 568/563
[58] Field of Search ........... 260/610 R, 610 D, 610 B, 260/338; 568/558, 563

[56] References Cited

U.S. PATENT DOCUMENTS

| 3,117,166 | 1/1964 | Harrison et al. ................. 260/610 R |
| 3,579,541 | 5/1971 | Chang ................................... 260/338 |

FOREIGN PATENT DOCUMENTS

| 50-22953 | 4/1975 | Japan .................................... 260/610 R |
| 936008 | 9/1963 | United Kingdom ................ 260/610 R |
| 1329859 | 9/1973 | United Kingdom ................ 260/610 R |

*Primary Examiner*—Werren B. Lone
*Attorney, Agent, or Firm*—Townsend and Townsend

[57] ABSTRACT

High density polyethylene is cross-linked with certain cyclic perketals including a group of novel cyclic perketals. Typical of the novel molecules is 3,6,6,9,9-pentamethyl-3-ethylacetate-1,2,4,5-tetraoxy cyclononane.

3 Claims, No Drawings

CYCLIC PERKETALS AND THEIR USE FOR CROSS-LINKING HIGH DENSITY POLYETHYLENE

This is a divisional application of copending application Ser. No. 772,407 filed Feb. 28, 1977, which in turn is a divisional of copending application Ser. No. 688,874 filed May 21, 1976, which in turn is a continuation-in-part of application Ser. No. 591,783 filed June 30, 1975, both now abandoned.

BACKGROUND OF THE INVENTION

1. Field of the Invention

This invention relates to an improved composition and process for making cross-linked high density polyethylene (HDPE) with certain cyclic perketals. Included within the useful cyclic perketals are a group of novel molecules.

2. Prior Art

Cyclic diperoxy ketals are disclosed in British Pat. Nos. 936,008 and 1,329,859; U.S. Pat. Nos. 3,117,166, 3,579,541 and 3,763,275; and Japanese patent publication No. 22953/1974.

The cross-linking of polyethylene including high density polyethylene with organic peroxides is disclosed in U.S. Pat. Nos. 3,118,866, 3,436,371 and 3,846,396.

U.S. Pat. No. 3,436,371 describes the process limitations and difficulties in employing organic peroxides for cross-linking high density polyethylene. For example, it is pointed out that there is a small tolerance between the minimum temperature at which effective blending of the polyethylene and peroxide cross-linking agent may be accomplished and the temperatures at which curing begins to take place at a rate which does not afford enough time for effective blending and forming. To overcome this difficulty the patent describes the use of a modifier in combination with dicumyl peroxide cross-linking agents. U.S. Pat. No. 3,118,866 also acknowledges these same difficulties to be overcome in cross-linking high density polyethylene with organic peroxides and suggests a particular class of peroxides for accomplishing such a purpose.

SUMMARY OF THE INVENTION

The present invention provides a novel composition and process for making cross-linked high density polyethylene which permits effective blending and forming and thereafter efficiently causes cross-linking. The composition includes high density polyethylene blended with an effective amount or organic peroxide for the cross-linking thereof. The organic peroxide has the formula:

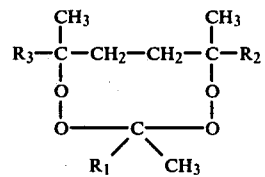

wherein each of $R_2$, $R_3$, $R_4$ and $R_5$ is selected from alkyl having from 1-4 carbon atoms; each of R and $R_1$ is selected from alkyl, hydroxy alkyl and alkyl carboxylate ester groups having up to about 10 carbon atoms,

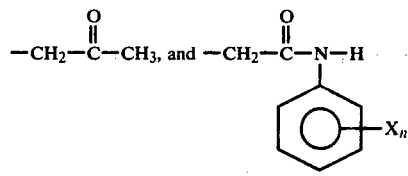

where n=0 to 3 and X is lower alkyl or alkoxy of up to about 5 carbon atoms; provided not more than one of R and $R_1$ is methyl when all of $R_2$, $R_3$, $R_4$ and $R_5$ are methyl. In the case of alkyl carboxylate ester groups, the carbon atom from the $R_1$ group which is attached to the methylenediperoxy carbon atom in the ring may be from either side of the carbonyl group in the ester, that is, either from the alcohol side or the carboxylic acid side of the ester.

The process of this invention is carried out under conventional conditions for cross-linking polyethylene with an organic peroxide. Thus the high density polyethylene is mixed with the above defined organic peroxide, the peroxide constituting about 0.001–10% by weight of the high density polyethylene, and the mixture is subjected to sufficient heat to cause cross-linking.

Within the group of cyclic perketals defined above as suitable for cross-linking high density polyethylene, a novel group of molecules has been discovered having the formula:

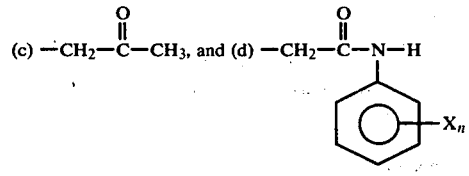

wherein each of $R_2$ and $R_3$ is selected from methyl and ethyl; $R_1$ is selected from (a) 2-methyl-2-hydroxy propyl, (b) alkyl carboxylate ester groups of up to about 10 carbon atoms,

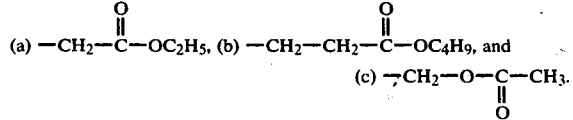

where n=0 to 3 and X is lower alkyl or alkoxy of up to about 5 carbon atoms.

With respect to the novel molecules, certain ones include an alkyl carboxylate ester group on the number 3 carbon atom of the heterocyclic ring. Specific ester groups provided by this invention include the following ones:

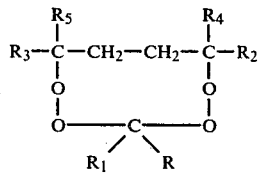

In this application these ester groups should be understood to be in a radical or de-protonated form for bonding to the number 3 carbon atom of the heterocyclic ring.

DETAILED DESCRIPTION OF THE INVENTION

The novel molecules of this invention are made in accordance with the following general reaction between a ketone and an alkyl dihydroperoxide.

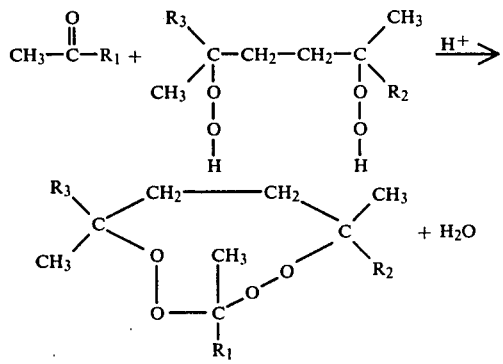

To make any of the novel molecules herein claimed (as well as any of the other cyclic perketals used in the cross-linking process of this invention) it is simply a matter of selecting the appropriate ketone and dihydroperoxide and employing it in a procedure such as the one below in which 3,6,6,9,9-pentamethyl 3-ethylacetate-1,2,4,5 tetraoxy cyclononane is prepared.

EXPERIMENTAL 20.97 g of 95.4% 2,5-dimethyl-2,5-dihydroperoxy hexane (0.112 mole) was dissolved in 65.7 g ethyl acetoacetate (0.505 mole) and 20 g isopropyl acetate as a solvent at 17° C. Then 1.5 g of 35% $H_2SO_4$ (0.05 mole) was added dropwise in 2 minutes to the stirred mixture. The temperature was raised, and the reaction stirred for 5 hours at 30°–35° C. Then 30 ml of benzene was added, and the reaction mixture was transferred to a separatory funnel. The isolated product layer was washed 3 times with 100 ml 3% NaOH solution and then 2 times with 100 ml 7% NaCl solution. Finally, the product was filtered through a cake of anhydrous $Na_2SO_4$ to remove all the water and concentrated under vacuum using a 35° C. water bath. A liquid product weighing 24.15 g was recovered. 1 R analysis indicated ester carbonyl absorption at 1733 $cm^{-1}$ and peroxide absorption at 858 and 881 $cm^{-1}$. The ketone carbonyl absorption at 1645 $cm^{-1}$ and hydroperoxide absorption at 3400 $cm^{-1}$ was not present. Product A.O. analysis: Theory, 11,02; Found, 11.00, 11.04, 99.8% pure; 73.9% yield.

The peroxides shown in Table 1 below are made by the above procedure by substituting the various ketones shown in the Table together with appropriate adjustment of mole ratios. When using the lower molecular weight ketone starting materials, the above experimental procedure may be further modified by omitting the isopropyl acetate solvent.

Table I

A. Cyclic Perketals Made From 2,5-dimethyl-2,5-Dihydroperoxy Hexane 6,6,9,9-Tetramethyl-3R-3R₁-1,2,4,5-Tetraoxycyclononane

| Starting Ketone | Group R | R₁ | Molec. Wt. | Theoretical Active Oxygen | 10 Hr. Half-Life Temp., °C.[1] | Synthesis Result % Yield | % Purity |
|---|---|---|---|---|---|---|---|
| 1. Dimethyl ketone | methyl | Methyl | 218.29 | 14.66 | 133 | 70.8 | 96.6 |
| 2. Cyclohexane | | R + R₁ = cyclohexyl | 258.35 | 12.39 | 122.5 | 92.7 | 95.0 |
| 3. Acetophenone | methyl | phenyl | 280.35 | 11.41 | 139.5 | 40.8 | 95.2[2] |
| 4. Methyl ethyl ketone | methyl | ethyl | 232.31 | 13.77 | 129 | 73.5 | 97.4 |
| 5. Methyl n-butyl ketone | methyl | butyl | 260.36 | 12.29 | 130 | 67.3 | 95.1 |
| 6. Diethyl ketone | ethyl | ethyl | 246.34 | 12.99 | 122.3 | 64.4 | 98.8 |
| 7. Ethyl isoamyl ketone | ethyl | 2-methyl butyl | 288.42 | 11.10 | 116.5 | 26.5 | 95.3 |
| 8. 4-Heptanone | propyl | propyl | 274.39 | 11.66 | 121.5 | 38 | 97.7 |
| 9. Ethyl acetoacetate | methyl | —CH₂—C(=O)—OC₂H₅ | 290.35 | 11.02 | 139 | 73.9 | 99.8 |
| 10. n-Butyl levulenate | methyl | —CH₂—CH₂—C(=O)—OC₄H₉ | 332.43 | 9.63 | 136.8 | 87.2 | 83.4 |
| 11. 4-methyl-4-methoxy-pentanone-2 | methyl | 2-methyl-2-methoxy propyl | 290.39 | 11.02 | 127 | 31.9 | 92.9 |
| 12. Hydroxy acetone[3] | methyl | hydroxy methyl | 233.92 | 13.68 | 104 | — | 97.33 |
| 13. Diacetone alcohol | methyl | 2-methyl-2-hydroxy propyl | 276.36 | 11.58 | 123.5 | 28.8 | 89.99 |
| 14. 3,3,5-Trimethyl cyclohexanone | | R + R₁ = 3,3,5-trimethyl cyclohexyl | 300.44 | 10.65 | 122.5 | 70.7 | 89.20 |
| 15. Acetoxy acetone | methyl | —CH₂—O—C(=O)—CH₃ | 276.32 | 11.58 | — | 35.7 | 96.55 |
| 16. 2,4-Pentanedione | methyl | —CH₂—C(=O)—CH₃ | 260.32 | 12.29 | 134 | 44.1 | 92.54 |

Table I-continued

| | | | | | | | |
|---|---|---|---|---|---|---|---|
| 17. Acetoacetanilide | methyl | 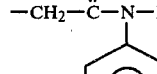 | | 337.40 | 9.48 | 139 | 78.4 | 98.01 |

B. Cyclic Perketals Made From 3,6-Dimethyl-3,6-Dihydroperoxy Octane

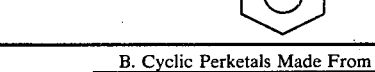

6,9-Diethyl-6,9-Dimethyl-3R-3R$_1$-1,2,4,5-Tetraoxy cyclononane

| | | | | | | | |
|---|---|---|---|---|---|---|---|
| 18. Dimethyl ketone | methyl | methyl | | 246.35 | 12.99 | 139.5 | 53.2 | 83.60 |
| 19. Methyl n-butyl ketone | methyl | butyl | | 288.42 | 11.10 | 124 | 67.7 | 85.16 |
| 20. Ethyl acetoacetate | methyl | 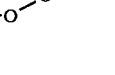 | | 318.40 | 10.05 | 126.5 | Unk[(4)] | 92.48 |

[(1)]Approximately 0.1M in Benzene
[(2)]Recrystallized
[(3)]Example 1, U.S. Pat. No. 3,579,541
[(4)]Losses during isolation In accordance with the present invention the cyclic perketals including the novel molecules of this invention are mixed or blended with high density polyethylene. High density polyethylene is defined in the prior art as having a density of about 0.94–0.96. (*Modern Plastics Encyclopedia* 1974–1975, page 82.) When the cyclic perketal is blended with such material cross-linking is accomplished by subjecting the mixture to a sufficient temperature, usually within a preferred range of about 150°–200° C. The amount of organic peroxide utilized is consistent with the prior art and will usually be in the range of about 0.001–10% by weight of the polyethylene.

In the preferred embodiment heating for purposes of cross-linking is applied during the procedure known as rotational molding. Rotational molding is a process intended primarily for the manufacture of hollow objects. In this process the solid or liquid polymer is placed in a mold; the mold is first heated and then cooled while being rotated about two perpendicular axes simultaneously. During the first portion of the heating stage when molding powdered material, a porous skin is formed on the mold surface. This gradually melts as the cycle progresses to form a homogenous layer of uniform thickness. However, when molding a liquid material, it tends to flow and coat the mold surface until the gel temperature of the resin is reached, at which time all flow ceases. The mold is then indexed into a cooling station, where forced air, water spray or a combination of both cool the mold. It is then positioned in a work zone, where the mold is opened, the finished part removed and the mold recharged for the following cycle. For more details as to the process and apparatus used in rotational molding see *Plastic Design And Processing*, February 1974, pages 19–23 and March 1974, pages 21–24.

In the preferred embodiment for rotational molding of high density polyethylene it is preferred to use cyclic perketals of the following formula:

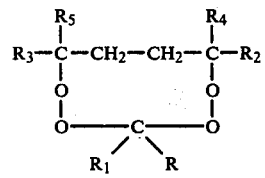

wherein each of $R_2$, $R_3$, $R_4$ and $R_5$ is selected from alkyl having from 1–4 carbon atoms; each of R and $R_1$ is selected from alkyl, hydroxy alkyl and alkyl carboxylate ester groups having up to about 10 carbon atoms,

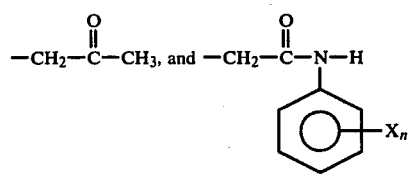

where n=0 to 3 and X is lower alkyl or alkoxy of up to about 5 carbon atoms; provided not more than one of R and $R_1$ is methyl when all of $R_2$, $R_3$, $R_4$ and $R_5$ are methyl, and where R and $R_1$ are alkyl, one of R and $R_1$ is methyl. These above perketals are desirable because they exhibit a satisfactory pot-life for rotational molding.

During the initial processing of high density polyethylene the organic peroxide is mixed and blended thoroughly with the polyethylene. To be satisfactory the organic peroxide should not cause excessive premature cross-linking during this phase of the processing. The cross-linking is desired only upon actual molding of the blended polyethylene. The following experimental work is designed to show the satisfactory pot-life obtainable with the cyclic perketals of this invention. In this work the equipment used simulates the milling or commonly used Banbury mixing step wherein all the ingredients such as anti-oxidants, fillers and the like which are normally added are mixed into molten polyethylene. Following this mixing step the blended material is conventionally sheeted out and pelletized or ground into a powder for later use in a mold such as a rotational molder or an extruder. More specifically, the data in Table II below was obtained utilizing the following procedure.

A Brabender Plasticorder with a Roller-5 type mixing head at a rotor speed of 30 RPM was used for these tests. Test conditions were:

A mixing head temperature of 160° C. was used. The resin used was Sode'fine Manolene ER63ONS HDPE (density range equals 0.946–0.968 g/cc; melt index equals 30). For these tests, 40.00 g of powdered resin was added directly to the mixing head. After 15 minutes, the desired amount of peroxide diluted in n-hexane was added by a syringe to the mixing head. The maximum torque reached in 65 minutes (50 minutes net) was recorded, and the run terminated. Net torque is equal to the maximum torque reached in 65 minutes minus the torque of virgin resin at 65 minutes. Each peroxide was tested twice.

ever, even peroxides 10, 11 and 12 demonstrate suitable properties for cross-linking high density polyethylene during molding procedures.

Table II indicates those types of cyclic perketals which demonstrate satisfactory pot-life properties so as to be useful for cross-linking high density polyethylene. While a cyclic perketal may have a suitable pot-life, in order to function in the process of this invention it must additionally effect the desired cross-linking reaction. The following experimental work illustrates the types of cyclic perketals which are effective cross-linking agents for high density polyethylene.

Tables III and IV below illustrate the effectiveness of the molecules of this invention. The data in Table III was generated by causing cross-linking to occur by press molding in accordance with the following procedure. Effectiveness for cross-linking is reported in terms of percent of cross-linking by the conventionally used percent gel test for determining the degree of cross-link- Table II Pot-Life of Various Cyclic Perketals in HDPE Using the Brabender Plasticorder at 160° C. Compared to Commercial Peroxides Each Peroxide used at a Molar Active Oxygen Equivalent to 1 phr 2,5-Dimethyl-2,5-Di-t-butyl peroxy Hexyne-3

| Peroxide | phr Used[1] | Net Torque, Mg[2] |
|---|---|---|
| 1. 2,5-Dimethyl-2,5-di-t-butyl peroxy hexyne-3 | 1 | 570 |
| 2. α,α'-Bis(t-butyl peroxy) diisopropyl benzene | 1.17 | 4685[3] |

| A. Cyclic Perketals Made From 2,5-Dimethyl-2,5-Dihydroperoxy Hexane | | | | |
|---|---|---|---|---|
| Starting Ketone | Group R | Group $R_1$ | phr Used | Net Torque, Mg. |
| 3. Hydroxy acetone | methyl | hydroxy methyl | 0.82 | 3858[4] |
| 4. Acetone | methyl | methyl | 0.76 | 362 |
| 5. Methyl ethyl ketone | methyl | ethyl | 0.81 | 625 |
| 6. Methyl n-butyl ketone | methyl | butyl | 0.91 | 477 |
| 7. Diacetone alcohol | methyl | 2-methyl-2-hydroxy propyl | 0.965 | 732 |
| 8. Ethyl acetoacetate | methyl | $-CH_2-\overset{O}{\overset{\|}{C}}-OC_2H_5$ | 1.00 | 242 |
| 9. n-Butyl levulenate | methyl | $-CH_2-CH_2-\overset{O}{\overset{\|}{C}}-OC_4H_9$ | 1.16 | 217 |
| 10. Diethyl ketone | ethyl | ethyl | 0.86 | 1317 |
| 11. Ethyl isoamyl ketone | ethyl | 2-methyl butyl | 1.01 | 1272 |
| 12. 4-Heptanone | propyl | propyl | 0.96 | 1270 |
| 13. Cyclohexanone | | $R + R_1$ = cyclohexyl | 0.90 | 270 |

| B. Cyclic Perketals Made From 3,6-Dimethyl-3,6-Dihydroperoxy Octane | | | | |
|---|---|---|---|---|
| 14. Acetone | methyl | methyl | 0.86 | 162 |

[1] On a 100% purity basis
[2] 50 minutes after peroxide added compared to virgin resin
[3] Cross-linked in 25.3 min.
[4] Cross-linked in 19.4 min.

In the above Table II the first two peroxides are included for comparison purposes. Peroxide 1 is a commercially available material with a suggested use similar to that of this invention. Peroxide 2 is typical of prior art peroxides for cross-linking polyethylene such as those disclosed in U.S. Pat. No. 3,118,866.

As may be seen from the results in Table II, the cyclic perketal made from hydroxyacetone (Example 1, U.S. Pat. No. 3,579,541) is unsuitable because it cross-links the polyethylene at 160° C. It is also noted that peroxides 10, 11 and 12 have a substantially higher net torque value over the commercially available peroxide 1. In view of these properties peroxides 10, 11 and 12 may be less desirable for cross-linking high density polyethylene in a rotational molding process as compared with the other cyclic perketals of the present process. Howing in cross-linked polyethylene.

PRESS MOLDING OF HDPE (TABLE III)

The desired amount of peroxide was dry-blended into 30.00 g of powdered resin by stirring for 5 minutes with a spatula. The resin used was Sode'fine Manolene ER63ONS HDPE (density range equals 0.946–0.968 g/cc; melt index equals 30). Solid peroxides were dissolved in n-hexane and added to the resin in a round bottom flask. After mixing, the solvent was removed under reduced pressure using a rotating evaporator and a 40° C. water bath. Platen temperatures on the press were checked with a surface pyrometer and were 390°±5° F. Press time was varied from 15–30 minutes depending upon the peroxide used. Cure time started when the ram gauge read 1,000 PSIG. Final ram pressure was between 4,000–8,000 PSIG. It took 6 minutes to cool the press to 245°–250° F. (platen thermometers) and release the pressure. Trays were removed from the molds within two minutes and cooled quickly in a water bath.

To determine the %wt gel, approximately 0.3000 g sample was cut into 6–7 pieces and placed inside a stainless steel screen pouch. These pouches were extracted in 2 liters of boiling xylene containing 10 g of Plastanox 2246 anti-oxidant for 16 hours and then dried in an oven at 170° C. for 4 hours.

The %wt gel was calculated by the following formula:

$$\% \text{ wt gel} = \frac{W_1 - (W_2 - W_3)}{W_1} - 0.0036 \times 100$$

wherein:

$W_1$ = wt. of sample, g
$W_2$ = wt. of sample + screen, g
$W_3$ = wt. of sample + screen after extraction, g
0.0036 = blank value for resin without peroxide.

Table III

Cyclic Perketals Made From 2,5-Dimethyl-2,5-Dihydroperoxy Hexane and Tested as Cross-Linking Agents of HDPE 6,6,9,9-Tetramethyl-3R-3$R_1$-1,2,4,5-Tetraoxycyclononane

| | | Group | | Amt. Used | | % Wt Gel when Press Molded at 390° C. | |
|---|---|---|---|---|---|---|---|
| | Starting Ketone | R | $R_1$ | phr[1] | Moles ($\times 10^{-3}$) | Molded 15 Min. | Molded 30 Min. |
| 1. | Dimethyl ketone | methyl | methyl | (a) 0.76 | 3.48 | 1.8 | — |
| | | | | (b) 1.00 | 4.58 | 48.7 | — |
| 2. | Cyclohexanone | R + $R_1$ = cyclohexyl | | (a) 0.90 | 3.48 | 0 | — |
| | | | | (b) 1.50 | 5.81 | 0 | — |
| 3. | Acetophenone | methyl | phenyl | (a) 0.50 | 1.78 | 0 | — |
| | | | | (b) 0.75 | 2.68 | 0 | — |
| | | | | (c) 1.00 | 3.57 | 16.2 | — |
| | | | | (d) 1.50 | 5.35 | 46.6 | — |
| 4. | Methyl n-butyl ketone | methyl | butyl | (a) 0.75 | 2.88 | 93.7 | — |
| | | | | (b) 0.91 | 3.50 | 94.7 | — |
| | | | | (c) 1.50 | 5.76 | 95.8 | — |
| 5. | Diethyl ketone | ethyl | ethyl | (a) 0.75 | 3.04 | 93.5 | — |
| | | | | (b) 0.86 | 3.49 | 95.5 | — |
| | | | | (c) 1.50 | 6.09 | 97.1 | — |
| 6. | Ethyl acetoacetate | methyl | —$CH_2$—C(=O)—O—$C_2H_5$ | (a) 0.50 | 1.72 | 12.5 | — |
| | | | | (b) 0.75 | 2.58 | 73.9 | 86.4 |
| | | | | (c) 1.00 | 3.44 | 91.3 | 84.0 |
| | | | | (d) 1.25 | 4.31 | 92.2 | 90.5 |
| | | | | (e) 1.50 | 5.17 | 93.1 | 92.2 |
| 7. | n-Butyl levulenate | methyl | —$CH_2$—$CH_2$—C(=O)—$OC_4H_9$ | (a) 0.75 | 2.26 | 23.3 | 28.4 |
| | | | | (b) 1.16 | 3.49 | 48.8 | — |
| | | | | (c) 1.50 | 4.51 | 84.3 | 87.3 |
| 8. | 2,5-dimethyl-2,5-Di(t-butylperoxy)Hexyne-3[2] | — | — | (a) 0.50 | 1.75 | 96.3 | — |
| | | | | (b) 0.75 | 2.62 | 98.5[3] | — |
| | | | | (c) 1.00 | 3.49 | 99.0 | — |
| 9. | Blank, Resin only | — | — | (a) None | — | 0.4 | — |

[1]On a 100% purity basis
[2]A commercial dialkyl peroxide normally used to cross-link HDPE
[3]Molded 10 min.

The data in Table IV below is also offered to show effectiveness in cross-linking. In this instance results are reported in terms of net torque as measured in a Torque Rheometer. As with the data in Table II, a Brabender Plasticorder with a Roller-5 type mixing head at a rotor speed of 30 RPM was used for these tests.

A mixing head temperature of 180° C. was used. The resin used was Phillips Marlex BMN 5565 HDPE (density equals 0.955 g/cc; melt index equals 6.5). The same weight of resin was used, and same procedure followed as with Table II, except the diluted peroxide was added at 16 minutes. If the maximum torque was not reached in 76 minutes (60 minutes net), the run was terminated. Net torque is equal to the maximum torque minus the torque at 16 minutes. Time to reach maximum torque is the time at maximum torque minus 16 minutes.

Table IV

A. Cyclic Perketals Made From 2,5-Dimethyl-2,5-Dihydroperoxy Hexane and Tested as Cross-Linking Agents of HDPE Using the Brabender Plasticorder at 180° C. & 200° C.

Table IV-continued

6,6,9,9-Tetramethyl-3R-3R$_1$-1,2,4,5-Tetraoxycyclononane

| | Group | | Amt. Used | | Net Torque, Mg[2] Head Temp., °C. | | Time to Reach Maximum Torque, Min. | |
|---|---|---|---|---|---|---|---|---|
| Starting Ketone | R | R$_1$ | phr[1] | Moles (×10$^{-3}$) | 180 | 200 | 180 | 200 |
| 1. Dimethyl ketone | methyl | methyl | (a) 0.5 | 2.29 | 665 | 2010, | 60.0[3] | 47.0, 48.3 |
| | | | (b) 1.0 | 4.58 | 790 | — | 60.0[3] | — |
| 2. Cyclohexanone | | R + R$_1$ = cyclohexyl | (a) 0.5 | 1.94 | 615 | — | 60.0[3] | — |
| | | | (b) 1.0 | 3.87 | 1000 | — | 60.0[3] | — |
| 3. Acetophenone | methyl | phenyl | 0.5 | 1.78 | 570 | — | 60.0[3] | — |
| 4. Methyl ethyl ketone | methyl | ethyl | 0.5 | 2.15 | (a) 2010 | — | 45.3 | 13 |
| | | | | | (b) 2065 | — | 44.0 | — |
| 5. Methyl n-butyl ketone | methyl | butyl | 0.5 | 1.92 | 2440 | 4000 | 39.0 | 17.5 |
| 6. Diethyl ketone | ethyl | ethyl | 0.5 | 2.03 | 2735 | — | 35.0 | — |
| 7. Ethyl isoamyl ketone | ethyl | 2-methyl butyl | 0.5 | 1.73 | 1990 | — | 12.0 | — |
| 8. 4-Heptanone | propyl | propyl | 0.5 | 1.82 | 3250 | — | 27.8 | — |
| 9. Ethyl acetoacetate | methyl | —CH$_2$—C(=O)—OC$_2$H$_5$ | (a) 0.5 | 1.72 | 1980 | 3050 | 56.4 | 28.3 |
| | | | (b) 1.0 | 3.44 | 3200 | — | 36.6 | — |
| 10. n-Butyl levulenate | methyl | —CH$_2$—CH$_2$—C(=O)—OC$_4$H$_9$ | (a) 0.5 | 1.50 | 1240 | — | 60.0[3] | — |
| | | | (b) 1.0 | 3.01 | 1855 | — | 54.0 | — |
| 11. 2,5-Dimethyl-2,5-Di(t-butyl peroxy)Hexyne-3[4] | — | — | 0.5 | 1.75 | 1935 | — | 26.0 | — |
| 12. 4-Methyl-4-methoxy pentanone-2 | methyl | 2-methyl-2-methoxy propyl | (a) 0.5 | 1.72 | 365 | — | 40.0[5] | — |
| | | | (b) 0.85 | 2.93 | 305 | — | 40.0[5] | — |
| | | | (c) 0.85 | 2.93 | 370 | — | 40.0[5] | — |
| 13. Diacetone alcohol | methyl | 2-methyl-2-hydroxy propyl | (a) 0.5 | 1.18 | 1470 | — | 17.2 | — |
| | | | (b) 1.0 | 3.62 | 4400 | — | 17.5 | — |
| 14. 3,3,5-Trimethylcyclohexanone | | R + R$_1$ = 3,3,5-trimethyl cyclohexyl | 0.5 | 1.66 | 440 | — | 60.0[3] | — |
| 15. Acetoxy acetone | methyl | —CH$_2$—O—C(=O)—CH$_3$ | 0.5 | 1.81 | 2700 | — | 39.7 | — |
| 16. 2,4-Pentanedione | methyl | —CH$_2$—C(=O)—CH$_3$ | 0.5 | 1.92 | 1880 | 3540 | 49.5 | 20.8 |
| 17. Acetoacetanilide | methyl | —CH$_2$—C(=O)—N—H—C$_6$H$_5$ | (a) 0.5 | 1.48 | — | 1770, | — | 18.5, 19.0 |
| | | | (b) 0.77 | 2.29 | — | 1655 2330 | — | 16.5 |

B. Cyclic Perketals Made From 3,6-Dimethyl-3,6-Dihydroperoxy Octane 6,9-Diethyl-6,9-Dimethyl-3R-3R$_1$-1,2,4,5-Tetraoxy cyclononane

| Starting Ketone | R | R$_1$ | phr[1] | Moles (×10$^{-3}$) | 180 | 200 | 180 | 200 |
|---|---|---|---|---|---|---|---|---|
| 18. Dimethyl ketone | methyl | methyl | (a) 0.5 | 2.03 | 1795 | — | 60.0[3] | — |
| | | | (b) 1.0 | 4.06 | 3315 | — | 35.7 | — |
| | | | (c) 1.0 | 4.06 | 3445 | — | 36.0 | — |
| 19. Methyl n-butyl ketone | methyl | butyl | 0.5 | 1.73 | 1850 | — | 50.0 | — |
| 20. Ethyl acetoacetate | methyl | —CH$_2$—C(=O)—OC$_2$H$_5$ | (a) 0.5 | 1.57 | 1120 | — | 60.0[3] | — |
| | | | (b) 1.0 | 3.14 | 2615 | — | 45.8 | — |

[1]Parts per 100 parts resin, on a 100% purity basis
[2]Meter-grams
[3]Run terminated 60 min. after peroxide added
[4]A commercial dialkyl peroxide normally used to cross-link HDPE
[5]Run terminated 40 min. after peroxide added Of the cyclic perketals made from 2,5-dimethyl-2,5-dihydroperoxy hexane which survive the pot-life test, the following ones fall to cross-link HDPE as may be seen in Tables III and IV:

| | Group | |
|---|---|---|
| Starting Ketone | R | R$_1$ |
| 1. Acetone | methyl | methyl |
| 2. Cyclohexanone | R + R$_1$ = cyclohexyl | |
| 3. 3,3,5-Trimethyl Cyclo hexanone | R + R = 3,3,5-trimethyl cyclohexyl | |
| 4. Acetophenone | methyl | phenyl |
| 5. 4-methyl-4-methoxy pentanone-2 | methyl | 2-methyl-2-methoxy propyl |

Surprisingly, the cyclic perketal made with diacetone alcohol (4-hydroxy-4-methyl pentanone-2) works well.

All three cyclic perketals made from 3,6-dimethyl-3,6-dihydroperoxy octane work well, including the one made from acetone.
We claim:
1. An organic peroxide of the formula:
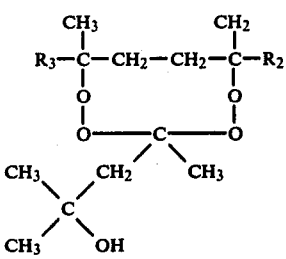
wherein each of $R_2$ and $R_3$ is selected from methyl and ethyl.
2. The organic peroxide of claim 1 wherein $R_2$ and $R_3$ equal methyl.
3. The organic peroxide of claim 1 wherein $R_2$ and $R_3$ equal ethyl.
* * * * *